United States Patent [19]

Banko et al.

[11] Patent Number: 4,719,907

[45] Date of Patent: Jan. 19, 1988

[54] ORTHOPEDIC PIN PLACEMENT GUIDE

[75] Inventors: Victor F. Banko, Dover, N.J.; Robert E. Zickel, Hastings on the Hudson, N.Y.

[73] Assignee: Orthospec, Inc., Spring Valley, N.Y.

[21] Appl. No.: 27,301

[22] Filed: Mar. 18, 1987

[51] Int. Cl.$^4$ ............................................. A61F 5/04
[52] U.S. Cl. .............................. 128/92 VD; 128/92 V
[58] Field of Search .......... 128/92 VD, 92 V, 92 YK, 128/92 YV, 92 R

[56] References Cited

U.S. PATENT DOCUMENTS

| | | | |
|---|---|---|---|
| 3,171,408 | 3/1965 | Childs et al. | |
| 3,765,034 | 10/1973 | Johnston | 128/92 VD |
| 3,842,824 | 10/1974 | Neufeld | |
| 4,360,012 | 11/1982 | McHarrie et al. | 128/92 ZW |
| 4,488,543 | 12/1984 | Tornier | |
| 4,522,201 | 6/1985 | Tongue | |
| 4,570,624 | 2/1986 | Wu | |

*Primary Examiner*—C. Fred Rosenbaum
*Assistant Examiner*—C. W. Shedd
*Attorney, Agent, or Firm*—Lerner, David, Littenberg, Krumholz & Mentlik

[57] ABSTRACT

A guide device for the placement of a bone screws or pin in the orthopedic treatment of bone fractures is disclosed. The guide device is constructed of a body having one or more tunnels for guiding therethrough an orthopedic pin for placement in the orthopedic treatment of a bone fracture. The body includes at least one frangible portion for separating the body from about the pin such that the body is removable while the pin remains in secured place within the bone.

20 Claims, 5 Drawing Figures

ORTHOPEDIC PIN PLACEMENT GUIDE

FIELD OF THE INVENTION

This invention relates in general to the treatment of bone fractures, and more particularly, to an orthopedic pin placement guide for precision guiding bone screws or pins into fractured bone to promote healing.

BACKGROUND OF THE INVENTION

Skeletal fractures are common injuries. These fractures are commonly debilitating and often require the patient to undergo surgery. Indeed, some fractures provide such difficulty for the orthopedic surgeon that complete prostetic replacements are called for. Even when such drastic measures as complete replacement are not necessary, the proper setting of a fractured bone poses substantial challenges to the most skilled orthopedic surgeon.

The difficulties faced by an orthopedic surgeon in properly reducing a fracture are well-known. These difficulties include dealing with the complex shape of many bones when aligning the fracture and the concommitant difficulties in proper placement of an orthopedic pin or pins for holding the fracture fragments in appropriate alignment for healing. This latter problem of parallel pin or bone screw alignment remains one of the challenges facing an orthopedic surgeon in fracture surgery.

There is known to the orthopedic surgeon a variety of guides which facilitate orthopedic pin placement in bone fracture surgery, for example, as disclosed in U.S. Pat. Nos. 4,570,624 and 3,171,408. The use of such guides has substantially assisted the orthopedic surgeon in both appropriately aligning a fracture and in correctly placing the orthopedic pins in the parallel fashion necessary to insure proper healing of the fracture. However, where orthopedic pins having enlarged heads are used, as is typical, a problem is encountered in removing the guide without disturbing the precision alignment of the pins. In the past, this problem was overcome with complex assemblies which did not require frangibility and which were difficult, cumbersome, unreliable, and costly to use. It is, therefore, one object of this invention to provide an orthopedic pin placement guide designed to permit its easy removal subsequent to proper bone alignment and pin placement.

Another object of this invention is to provide an orthopedic pin placement guide for precision placement of pins into fractured bones for therapeutic purposes.

Another object of this invention is to provide an orthopedic pin placement guide having weakened areas to promote frangibility.

Another object of this invention is to provide an orthopedic pin placement guide designed so that the guide breaks along frangible portions about the placed orthopedic pins thereby not disturbing or in any way damaging the pins or their precision alignment.

Another object of this invention is to provide an orthopedic pin placement guide providing easy visualization of pin placement.

Another object of this invention is to provide an orthopedic pin placement guide which permits proper placement of orthopedic pins so that they are substantially parallel and thus provide for proper healing of the fractures.

SUMMARY OF THE INVENTION

Disclosed is a guide for orthopedic pin placement in treatment of human bone fractures. The guide comprises a plurality of pin placement tunnels for placing a pin therethrough having a designated alignment for parallel pin placement. Preferably, the tunnels are angulated appropriately angle for bone healing. As an example, in the case of a femoral neck fracture the angle corresponds to the angle subtended by the femoral neck and femoral shaft.

The top side of the guide includes a trough-like depression within which a substantial portion of the pin placement tunnel entry points are located. The lines or curves on the topside are such as to allow conformance to the appropriate bone surface anatomy. The curved end may commonly be rounded such that it conforms to the curved end of the fractured bone. The guide further includes frangible portions to facilitate the breaking and removal of the guide from the bone after placement of the orthopedic pins. The tunnels of the guide are set at an angle to facilitate proper bone healing. In the example of a fractured femoral neck the tunnel angles are between 125° and 150° and most preferably between 130° and 140°. These tunnels must be sufficient in number and spaced so as to properly position the bone screws or pins. Further, the guide is preferably clear or transparent to permit visualization for the surgeon of pin placement in the tunnels. This visualization may easily take place if the guide is made of a transparent material such as acrylic. Also facilitating ease of use of the guide for the surgeon is that the guide can be made from lightweight, disposable material which is biocompatible.

The frangible portions of the guide interconnect to form a web. The web is located on the guide such that it intersects with the pin placement tunnels thereby insuring that the frangible portions intersect the pin placement tunnels. Ideally, the frangible portions include a hollowed out portion or slot such that only securing means bridge the frangible portions holding the guide together.

In accordance with one embodiment of the invention, a guide device for the placement of a pin in the orthopedic treatment of bone fractures is disclosed. The guide is constructed of a body having an opening for guiding therethrough a pin for placement in the orthopedic treatment of a bone fracture. The body includes a frangible portion for separating the body from about the pin whereby the body is removable while the pin remains in place within the bone.

BRIEF DESCRIPTION OF THE FIGURES

The above description, as well as further objects, features and advantages of the present invention will be more fully understood by reference to the following detailed description of a presently preferred, but nonetheless illustrative, orthopedic pin placement guide in accordance with the present invention when taken in conjunction with the accompanying drawings wherein.

DETAILED DESCRIPTION

Figure 1:
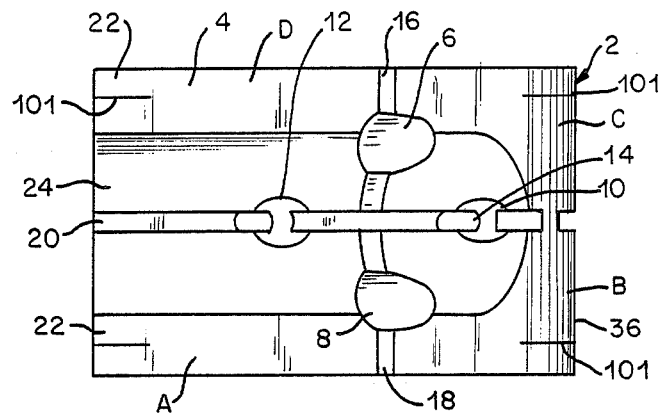
FIG. 1 is a top plan view of the guide depicting the entry points for the pin placement tunnels, the curved end of the guide, and the frangible portions.

The orthopedic pin placement guide disclosed herein is for use by an orthopedic surgeon or other medical professional in the treatment of bone fractures requiring placement of at least one orthopedic pin in a fractured bone. The guide is designed to make placement of at least one pin of the type used in orthopedic surgery as facil as possible. Most significantly, the guide is easily frangible thereby permitting easy removal of the guide upon successful placement of the orthopedic bone screws or pins. This frangibility is such that the guide breaks pursuant to designated frangible portions about the therapeutically placed pins without disturbing in any way the pin placement. Further, ease of frangibility minimizes, and in many cases eliminates, any additional trauma caused by the removal of prior orthopedic pin guides which were not frangible. As will be evidenced below, other aspects of this guide contribute to mitigating the difficulties faced by an orthopedic surgeon or other medical professional in pin placement.

Referring now to the drawings, wherein like reference numbers represent like elements, there is shown an orthopedic pin placement guide designated generally by reference number 2. The guide 2 is constructed from a body 4 having at least one pin placement tunnel although any number may be incorporated. In the embodiment shown in the figures, four pin placement tunnels are designated by reference numbers 6, 8, 10 and 12. The body 4 further includes open frangible portions designated by reference numbers 14 and 16 which divide the guide into four quadrants designated A, B, C, and D. Securing pieces 18 and 20 bridge the open frangible portions 14, 16 so as to hold the four quadrants A, B, C, and D together as an integral unit.

Figure 3:
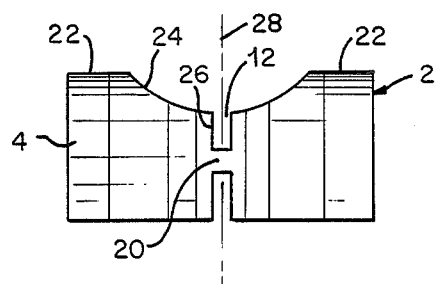
FIG. 3 is an end view of the guide showing the frangible portion with securing means holding the guide together.

On one side of body 4 there is provided a flat region 22 into which there is formed a trough-like depression 24 to provide facility and stability in placing the guide against the bone. The trough-like depression 24 is preferably a circular arc, as shown in FIGS. 1 and 3 in the case of a fractured femur, however, other geometries will equally provide facility and stability depending on the physical characteristics of the specific fracture. As will become apparent from the function of the trough-like depression 24, as to be described hereinafter, other shapes may be used.

Figure 2:
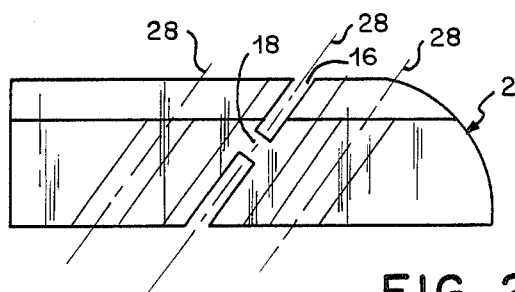
FIG. 2 is a side view of the guide showing the frangible portions conforming to the angle of the pin placement tunnels.

Through the body 4, as already described, there is at least one pin placement tunnel, e.g. 6, which has an angular orientation along the axis designated by reference number 28. Preferedly, a plurality of pin placement tunnels, e.g. 6, 8, 10 and 12, are used, although more or less are contemplated. As can be seen in FIG. 2, the pin placement tunnels 6, 8, 10, and 12 are parallel to each other, i.e. tunnels 6 and 8 are parallel to each other as well as to tunnels 10 and 12. It will, of course, be understood by one skilled in the art that the precise geometric shape made by the arrangement of the pin placement tunnels can be modified to meet the requirements of the fracture and the orthopedic surgeon. However, in a currently preferred embodiment the pattern envisioned is a triangular or rectangular but other patterns such as a straight line would be effective. The pin placement tunnels 6, 8, 10 and 12 may be adapted to receive any of a variety of orthopedic pins commonly used in the medical arts, especially those pins known as Knowles, Hagie, or Gouffon.

Figure 4:
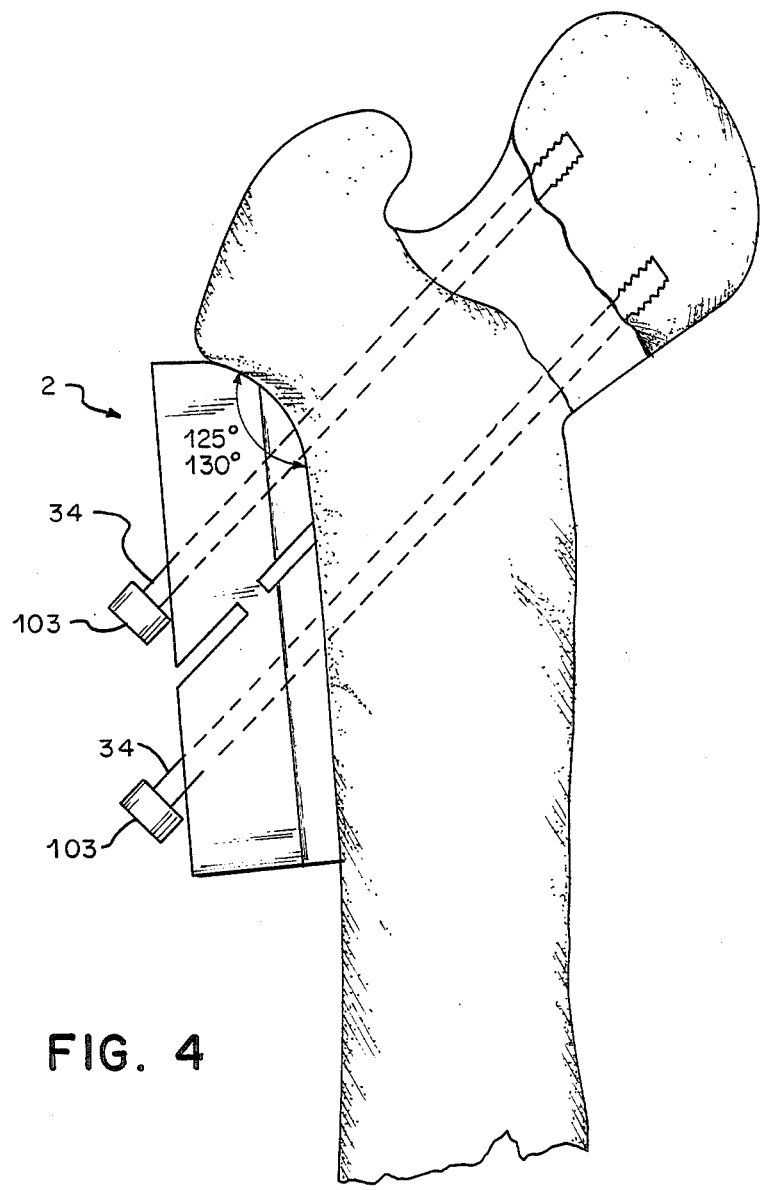
FIG. 4 is a perspective view showing the orthopedic pin placement guide in place against a bone being treated for a fracture.

Facilitating the removal of the guide following implantation of at least one orthopedic pin is the presence of the open frangible portions 14 and 16. These frangible portions 14 and 16 provide ease of frangibility in a manner which minimizes the chance of trauma to the bone. This frangibility is accomplished by breaking the guide into the plurality of quadrants A, B, C, and D about the pin placement tunnels 6, 8, 10 and 12, without disturbing the pins 34 which have been guided therethrough, as shown in FIG. 4. In so doing, the pins remain in the precise location and in the precise condition which the orthopedic surgeon desires.

The open frangible portions 14 and 16 may be in any pattern which provide for easy breaking of the guide following pin placement. In the currently preferred embodiment, the pattern is that of a cross in which each of the open frangible portions 14 and 16 intersect the parallel sets of pin placement tunnels 6, 8, 10 and 12. That is, as shown in FIG. 1, open frangible portion 14 intersects parallel pin placement tunnels 6 and 8 while open frangible portion 16 intersects pin placement tunnels 10 and 12. Further, it is preferred that these weakened areas, as exemplified by the open frangible portions 14 and 16, be formed in the body 4 to be congruent with the angles of the pin placement tunnels 6, 8, 10, and 12 so as to insure that breaking of the guide is facilitated. Frangible portion 16 shown in FIG. 2 represents such an angularly arranged frangible portion. Securing pieces 18 and 20 bridge the frangible portions 14 and 16 to insure that the guide 2 does not break until the orthopedic surgeon so desires. Upon breakage, the securing pieces 18 and 20 are cleaved, allowing the guide 2 to break apart along the open frangible portions 14 and 16 and into four quadrants A, B, C, and D. As can be seen from FIG. 1, the cross-like pattern formed by the open frangible portions 14 and 16 will result in the guide 2 breaking into the four quadrants following cleavage of the securing pieces 18 and 20. The pin placement device may optionally comprise radioopaque markers, shown as 101 pictorially shown in FIG. 1, in each of the aforesaid quadrants to facilitate identification and location of such quadrants by radiograph techniques such as X-rays.

Figure 5:
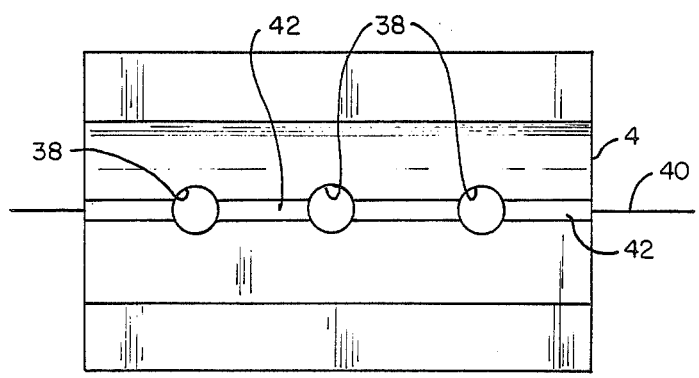
FIG. 5 is a top view showing an embodiment of an orthopedic pin placement guide having a parallel pin placement tunnels.

FIG. 4 demonstrates the precise angular position required by pin placement tunnels 6, 8, 10 and 12 when the instant guide 2 is used in the treatment of fractures of the human femoral neck. The guide 2 will therefore have a beveled edge 36 as shown in FIG. 1 facilitating placement of the guide on the broken bone. The pin placement tunnels 6, 8, 10, and 12 preferably define an angle of approximately 125°-150° as shown in FIG. 4, when measured from the underside of the greater trochanter. In the preferred embodiment, the angle of tunnels is between 130°-140°. Also shown in FIG. 4 is the use of enlarged heads 103 on the pins 34 used to secure the broken bone. It is, of course, understood that there can be variation in such angles given the wide variation of human skeletal structure. For instance, FIG. 5 shows the pin placement tunnels 38 parallel to each other and perpendicular to a longitudinal axis 40 which is parallel to the body 4. The frangible portions in this embodiment are indicated by the reference numeral 42. However, those skilled in the art will understand that the angular ranges stated defines the appropriate angle for the vast majority of humans but may vary in each patent.

In use, the orthopedic surgeon places the guide 2 in communication with the fractured bone requiring treatment. The surgeon determines this by ascertaining the precise spot in which he or she desires to place pin or pins 34 for treatment of the fracture. In the case of a fracture of the human femoral neck, the beveled edge portion 36 is placed so as to insure that the angle defined by the greater trochanter in the guide 2 is in the range defined above, and as exemplified in FIG. 4. The guide 2 is then placed in such a way so that the flat region 22 is in a position such that the orthopedic professional has easy access to the pin placement tunnels 6, 8, 10, and 12. The desired pins 34 are selected by the professional and placed within the pin placement tunnels 6, 8, 10, and 12. It will be noted from FIG. 1 that the mouth of the tunnels 6, 8, 10, and 12 are at least partially within the trough-like depression 24. This facilitates placement of the pins 34 into the mouth of the tunnels because the trough-like depression 24 guides the leading end of the pins 34 into the tunnels 6, 8, 10, and 12.

After the pins 34 have been appropriately placed in the bone so as to insure proper healing, the medical professional removes the guide 2. Removal is easily accomplished by exerting a force against the guide 2 to cause the open frangible portions 14 and 16 to cleave through the securing pieces 18 and 20 which serve to bridge the four quadrants A, B, C and D while the pins remain in place within the bone. If the guide 2 is of the embodiment shown in FIG. 1, such a cleavage will result in four distinct fragments given the cross-like pattern created by the open frangible portions 14 and 16. Following the cleavage of the frangible portions the pins are driven into the bone to the proper depth.

It will be understood that the guide 2 can be any shape, but preferably substantially rectangular in its overall configuration as generally shown in FIGS. 1, 3 and 5. One side of the guide 2 may be rounded or beveled as shown by reference number 36 to conform to the curvature of a designated bone. It is generally preferred that the beveling be accomplished so that the beveled surface is completely smooth and joins the flat region 22 without sharp edges. Sharp edges on the guide 2 could result in additional traumatization of the injured area.

Further making the guide 2 a greater benefit to orthopedic professionals is use of lightweight, inexpensive materials. Lightweight materials make the guide easy to manipulate, while the use of inexpensive materials substantially reduces the cost associated with use of the guide. Lastly, it is preferred that the materials used be clear, or at a minimum transparent, so that the orthopedic professional may look through the guide 2 while using it in order to ensure proper orientation of the guide with the bone and proper pin placement. It will be understood by some skilled in the art that the guide device be composed of a biocompatible material. In its currently preferred form, a material which comprises all these desirable features is acrylic.

It will be understood that the embodiments described herein are merely exemplary and that a person skilled in the art may make many variations and modifications without departing from the spirit and scope of the invention. All such modifications and variations are intended to be included from the scope of the invention as defined in the appended claims.

What is claimed is:

1. Guide device for the placement of a pin in the orthopedic treatment of bone fractures, said device comprising a body having a first opening for guiding therethrough a pin for placement in the orthopedic treatment of a bone fracture, said body having a frangible portion for separating said body from about said pin, whereby said body is removable while said pin remains in place within said bone.

2. The device of claim 1 wherein said first opening is a pin placement tunnel for guiding said pin into place during orthopedic treatment of a bone fracture.

3. The guide device of claim 1 wherein said first opening intersects said frangible portion.

4. The guide device of claim 3 further including a trough-like depression formed within said body and arranged in communication with said first opening.

5. The guide device of claim 3 further including a second opening, said second opening arranged parallel to said first opening for guiding therethrough a pin for placement in the orthopedic treatment of a bone.

6. The guide device of claim 5 wherein said frangible portion intersects said first opening and said second opening.

7. The guide device of claim 3 wherein said first opening is angularly arranged with respect to a longitudinal axis of said body.

8. The guide device of claim 7 wherein said frangible portion is at an angle corresponding to the angular arrangement of said first opening.

9. The guide device of claim 7 wherein the angular arrangement of said first opening is approximately between 125°–150° when measured from the underside of a human greater trochanter in the treatment of bone fractures of a human femoral neck.

10. The guide device of claim 9 wherein the angular arrangement is between 130°–140°.

11. The guide device of claim 9 wherein said body has a rounded edge conforming to the underside of the greater human trochanter.

12. The guide device of claim 3 wherein said body is sufficiently transparent to permit visualization of said pin as said pin passes through said first opening.

13. The guide device of claim 3 wherein said body is made of acrylic.

14. The guide device of claim 3 wherein said frangible portion is a hollowed out region having securing means bridging said hollowed out region for holding said body together.

15. The device of claim 3 wherein said body includes a flat region having a trough-like depression extending therefrom.

16. The device of claim 15 wherein said trough-like depression is a circular arc.

17. The device of claim 3 further comprising radioopaque markers.

18. The device of claim 3 wherein said first opening is arranged perpendicular to a longitudinal axis of said body.

19. The guide device of claim 18 wherein said body further includes a beveled edge, said beveled edge conforming to the curvature of the underside of a human greater trochanter.

20. Guide device for the placement of a pin in the orthopedic treatment of bone fractures said device comprising:

a body having a plurality of openings for guiding therethrough pins for placement in the orthopedic treatment of a bone fracture;

at least one frangible portion within said body for separating said body from about said pin, said frangible portion intersecting said plurality of openings; and a trough-like depression within said body, said frangible portion and said plurality of openings located at least partially within said trough-like depression.

* * * * *